United States Patent [19]

Hori et al.

[11] Patent Number: 5,663,261
[45] Date of Patent: Sep. 2, 1997

[54] FILM-FORMING RESIN AND HAIR CARE COSMETIC CONTAINING THE SAME

[75] Inventors: Naomi Hori; Takashi Oda; Takako Taya; Katsumi Mita, all of Tokyo, Japan

[73] Assignee: Kao Corporation, Tokyo, Japan

[21] Appl. No.: 582,391

[22] Filed: Jan. 3, 1996

[30] Foreign Application Priority Data

Feb. 21, 1995 [JP] Japan .................................. 7-031992

[51] Int. Cl.$^6$ .................... C08F 226/02; C08F 236/02; C08F 236/22; A61K 7/06
[52] U.S. Cl. .................... 526/307.2; 424/47; 424/70.1; 424/70.11; 424/70.122; 424/70.17; 526/304; 526/307; 526/307.5; 526/307.7
[58] Field of Search .................... 424/47, 70, 71, 424/70.17, 70.1, 70.11, 70.122; 526/307.2, 304, 307.5

[56] References Cited

U.S. PATENT DOCUMENTS

| | | | |
|---|---|---|---|
| 3,296,235 | 1/1967 | Zoebelein et al. | |
| 3,850,178 | 11/1974 | Schoenholz | 132/7 |
| 4,196,190 | 4/1980 | Gehman | 424/47 |
| 4,445,521 | 5/1984 | Grollier | 132/7 |
| 5,009,880 | 4/1991 | Grollier | 424/47 |
| 5,278,269 | 1/1994 | Mita et al. | |

FOREIGN PATENT DOCUMENTS 0 372 546  6/1990  European Pat. Off.

*Primary Examiner*—Fred Zitomer
*Attorney, Agent, or Firm*—Oblon, Spivak, McClelland, Maier & Neustadt, P.C.

[57] ABSTRACT

A film-forming resin which is a copolymer of (meth) acrylamide and (meth)acrylate monomers is disclosed. The film-forming resin can sustain a hair style over a prolonged period of time, even under high humidity, when used in a hair care product. Further, it is excellent in shampoo-washability and set-retaining power.

5 Claims, No Drawings

FILM-FORMING RESIN AND HAIR CARE COSMETIC CONTAINING THE SAME

FIELD OF THE INVENTION

This invention relates to a film-forming resin and a hair care product containing the same.

BACKGROUND OF THE INVENTION

Film-forming resins have been used in hair care products (hair sprays, set lotions, etc.) to provide them with a good styling power or a lasting set-retaining power. Examples of these film-forming resins include polyvinyl pyrrolidone, polyvinyl pyrrolidone/vinyl acetate copolymers and vinyl acetate/crotonic acid copolymers.

It is required that a film-forming resin used in a hair care product enables the retention of a hair style for a long time and can be easily washed away with a shampoo or water.

Among the known polymers, however, those which are soluble in water suffer from a problem of becoming tacky under a high humidity due to their high hygroscopicity. That is to say, none of them satisfies both of the requirements of being tack-free even under a high humidity and exhibiting a good shampoo-washability. To overcome these problems, attempts have been made to reduce the tackiness while giving up the achievement of good shampoo-washability or to make the tackiness less conspicuous by using oily components such as silicone oil together with the polymers.

Moreover, a film made of such a water-soluble film-forming resin is softened due to water absorption, which makes it difficult to sufficiently sustain the hair style under a high humidity. When such a film-forming resin is used as a styling resin in an aerosol spray, furthermore, there arises another problem. That is to say, the film-forming resin is less soluble in hydrocarbons (LPG) commonly employed as propellant and, therefore, the aerosol composition should contain a further solvent (ethanol, isopropyl alcohol, etc.) in an elevated amount. As a result, the mist particles thus sprayed become large and heavy, which makes good styling difficult. In this case, furthermore, the resin film on the surface of the hair tends to peel off (so-called flaking) due to, for example, brushing. In this case, the gloss of the hair is deteriorated.

The present inventors have previously found a film-forming resin capable of sustaining a good set-retaining power even under a high humidity and applied it for a patent (EP-A-372546 and U.S. Pat. No. 5,278,269 corresponding to JP-A-2-180911; the term "JP-A" as used herein means an "unexamined published Japanese patent application"). However, this film-forming resin also suffers from a problem that it becomes tacky under a high humidity due to water absorption. Thus it has been still necessary to blend a specific oily component therewith so as to improve the texture.

Accordingly, an object of the present invention is to provide a film-forming resin which remains tack-free even under a high humidity, is capable of sustaining the hair style for a prolonged period of time, can be easily washed away with a shampoo or water, gives a good finishing when employed in an aerosol spray composition as a film-forming resin and causes no peeling of the film from the surface of the hair due to brushing.

Under these circumstances, the present inventors have further conducted extensive studies. As a result, they have successfully found out that it becomes possible to solve the problems mentioned above, while maintaining the fundamental performance of the film-forming resin of JP-A-2-180911, by employing a low-molecular weight (meth) acrylamide monomer as a substitute for the (meth)acrylate monomer constituting the copolymer of JP-A-2-180911, thus completing the present invention.

SUMMARY OF THE INVENTION

Accordingly, the present invention provides a film-forming resin which is a copolymer consisting essentially of:

(a) from 30 to 80% by weight of a (meth)acrylamide monomer represented by the following formula (1):

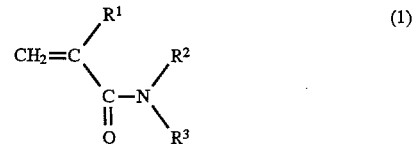

wherein $R^1$ represents a hydrogen atom or a methyl group; and $R^2$ and $R^3$ may be either the same or different and each represents a hydrogen atom or an alkyl group having 4 to 12 carbon atoms, provided that $R^2$ and $R^3$ do not represent hydrogen atoms at the same time;

(b) from 2 to 50% by weight of a (meth)acrylamide monomer represented by the following formula (2):

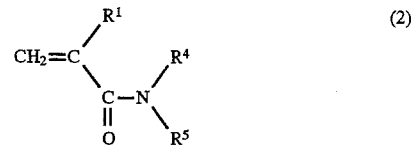

wherein $R^1$ is as defined above; and $R^4$ and $R^5$ may be either the same or different and each represents a hydrogen atom or an alkyl group having 1 to 3 carbon atoms;

(c) from 0 to 30% by weight of a (meth)acrylate monomer or a (meth)acrylamide monomer represented by the following formula (3):

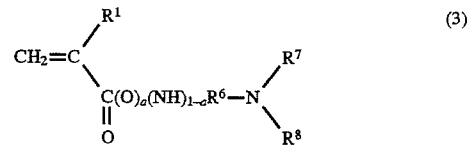

wherein $R^1$ is as defined above; $R^6$ represents an alkylene group having 2 or 3 carbon atoms; $R^7$ and $R^8$ may be either the same or different and each represents a methyl group or an ethyl group; and a represents a number of 0 or 1; and (d) from 0 to 40% by weight of a (meth)acrylate monomer represented by the following formula (4):

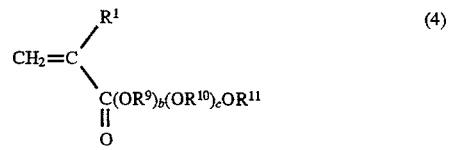

wherein $R^1$ is as defined above; $R^9$ and $R^{10}$ may be either the same or different and each represents an alkylene group having 2 to 4 carbon atoms; $R^{11}$ represents a hydrogen atom, an alkyl group having 1 to 10 carbon atoms or a phenyl group; and b and c represent each a number of from 0 to 50, provided that b and c do not represent 0 at the same time.

The present invention further provides a hair care product containing the above-mentioned film-forming resin.

DETAILED DESCRIPTION OF THE INVENTION

Examples of the (meth)acrylamide monomer (1) represented by the formula (1) to be used in the production of the film-forming resin of the present invention include N-n-butyl(meth)acrylamide, N-tert-butyl(meth)acrylamide, N-octyl(meth)acrylamide, N-lauryl(meth)acrylamide, N-1-metylundecyl(meth)acrylamide, N-2-ethylhexyl(meth) acrylamide and N-tert-octyl(meth)acrylamide. Among all, it is particularly preferable to use N-branched alkyl(meth) acrylamides such as N-tert-butyl(meth)acrylamide, N-tert-octyl(meth)acrylamide and N-2-ethylhexyl(meth) acrylamide therefor.

Either one of these monomers or a mixture thereof may be used in an amount of from 30 to 80% (by weight, the same will apply hereinafter), preferably from 40 to 70%, based on the total monomers.

Examples of the (meth)acrylamide monomer (2) represented by the formula (2) include (meth)acrylamide, N-methyl(meth)acrylamide, N-ethyl(meth)acrylamide, N-isopropyl(meth)acrylamide, N,N-dimethyl(meth) acrylamide and N,N-diethyl(meth)acrylamide. Among all, it is particularly preferable to use N-methyl(meth)acrylamide, N-ethyl(meth)acrylamide, N,N-dimethyl(meth)acrylamide and N,N-diethyl(meth)acrylamide therefor.

Either one of these monomers or a mixture thereof may be used in an amount of from 2 to 50%, preferably from 10 to 35%, based on the total monomers.

Examples of the (meth)acrylate and (meth)acrylamide monomers (3) represented by the formula (3) include N,N-dimethylaminoethyl (meth)acrylate, N,N-diethylaminoethyl (meth)acrylate, N,N-dimethylaminopropyl (meth)acrylate, N,N-dimethylaminopropyl(meth)acrylamide and N,N-diethylaminopropyl(meth)acrylamide.

Either one of these monomers or a mixture thereof may be used in an amount of from 0 to 30%, preferably from 0 to 10% and still preferably from 0.5 to 5%, based on the total monomers.

The monomer represented by the formula (4) is a (meth) acrylate having a polyoxyalkylene chain. In the formula (4), $R^{11}$ represents a hydrogen atom, an alkyl group having 1 to 10 carbon atoms or a phenyl group. It is preferable that $R^{11}$ is a hydrogen atom or an alkyl group having 1 to 4 carbon atoms, still preferably a methyl group. Examples of such a (meth)acrylate monomer (4) include hydroxyethyl (meth) acrylate, hydroxypropyl (meth)acrylate, polyethylene glycol mono(meth)acrylate, polypropylene glycol mono(meth) acrylate, methoxypolyethylene glycol mono(meth)acrylate, methoxypolypropylene glycol mono(meth)acrylate, ethoxypolyethylene glycol mono(meth)acrylate, butoxypolyethylene glycol mono(meth)acrylate and phenoxypolyethylene glycol mono(meth)acrylate. The polyoxyalkylene chain is a homopolymer or a copolymer of $C_2$–$C_4$ alkylene oxide(s). In the case of a copolymer, it may be a block copolymer or a random copolymer of ethylene oxide, propylene oxide, etc. The degree of polymerization of the alkylene oxide, which can be analyzed by gas chromatography, preferably ranges from 1 to 50 on average.

Either one of these monomers or a mixture thereof may be used in an amount of from 0 to 40%, preferably from 5 to 30% and still preferably from 10 to 25%, based on the total monomers.

The film-forming resin of the present invention can be produced by combining the above-mentioned monomers and copolymerizing them in the presence of a radical polymerization initiator by a known polymerization method; for example, bulk polymerization, solution polymerization, suspension polymerization or emulsion polymerization. It is particularly preferable to select the solution polymerization method therefor. It is preferable to use a water-miscible organic solvent optionally mixed with water as a solvent employed in the solution polymerization. Either one of such organic solvents or a mixture thereof may be used therefor. Examples of the water-miscible organic solvent include aliphatic alcohols having 1 to 3 carbon atoms (methanol, ethanol, propanol, etc.), ketones (acetone, methyl ethyl ketone, etc.) and ethers (tetrahydrofuran, glyme, diglyme, dioxane, etc.). Among all, it is preferable to use methanol, ethanol or acetone optionally mixed with water therefor.

Preferable examples of the radical polymerization initiator usable in the present invention include azo compounds such as 2,2'-azobisisobutyronitrile, 2,2'-azobis(2,4-dimethylvaleronitrile), 2,2'-azobis(4-methoxy-2,4-dimethylvaleronitrile), dimethyl-2,2'-azobisisobutyrate, 2,2'-azobis(2-methylbutyronitrile) and 1,1'-azobis(1-cyclohexanecarbonitrile). Also, use can be made of organic peroxides such tert-butyl peroctoate, dicumyl peroxide, di-tert-butyl peroxide and dibenzoyl peroxide therefor. However, such an organic peroxide is not preferable from an industrial viewpoint. This is because an organic peroxide might undergo a redox reaction with a tertiary amino group of the monomer (3), which makes it necessary to strictly regulate the reaction conditions, for example, performing the polymerization at a low temperature of 40° C. or below.

It is preferable to use the polymerization initiator in an amount of from 0.001 to 2.0% by mol, still preferably from 0.01 to 1.0% by mol, based on the monomer mixture.

The polymerization may be performed by feeding all of the monomers and the polymerization initiator followed by heating. Alternatively, each monomer and/or the polymerization initiator may be appropriately dropped or fed in portions.

The polymerization temperature may be appropriately determined depending on the radical polymerization initiator, monomers and solvent employed. It usually ranges from 30° to 100° C., preferably from 40° to 90° C. It is possible to perform the copolymerization in an inert gas atmosphere (for example, nitrogen atmosphere) as usually done in the art.

After the completion of the polymerization step, the copolymer can be separated from the polymerization mixture by a known method such as reprecipitation or distillation of the solvent. It is also possible to eliminate the unreacted monomers from the copolymer product by a known method such as repeated reprecipitation, membrane separation, chromatography or extraction.

The molecular weight (determined by gel filtration chromatography in terms of polyethylene glycol) of the copolymer thus obtained can be regulated to 1,000 to 1,000,000 by selecting appropriate polymerization conditions. In the present invention, it is preferably that the molecular weight of the copolymer ranges from 10,000 to 500,000, still preferably from 20,000 to 200,000.

Before using, the tertiary amino groups in the copolymer thus obtained may be neutralized with an inorganic acid or an organic acid to thereby impart a water solubility to the copolymer. In this case, it is preferable to neutralize 50 to 100%, still preferably 80 to 100%, of the total tertiary amino groups. The acid may be used in somewhat excess (i.e., an amount corresponding to 100 to 110% of the neutralization equivalent).

Examples of the inorganic acid usable herein include hydrochloric acid, sulfuric acid and phosphoric acid, while examples of the organic acid usable herein include acetic acid, glycolic acid, dimethylglycolic acid, lactic acid, dimethylolpropionic acid, tartaric acid, citric acid, maleic acid and malic acid.

Also, the amino groups in the copolymer can be quaternized with the use of an appropriate quaternizing agent. In this case, it is preferable to quaternize at least 50% of the total tertiary amino groups.

Examples of the quaternizing agent usable herein include dialkyl sulfates (dimethyl sulfate, diethyl sulfate, etc.), alkyl halides (methyl chloride, propyl bromide, benzyl chloride, etc.) and aralkyl halides.

Alternatively, such a quaternized copolymer can be obtained by quaternizing the monomer (3) with a quaternizing agent followed by copolymerization.

Examples of the hair care product containing the film-forming resin of the present invention include hair sprays, set foams, set lotions, gels, shampoos and rinses. It may be in various forms including aqueous solutions, aqueous alcoholic solutions, emulsions, creams and gels. These hair care products may be roughly classified into those containing propellants (hair sprays, set foams, etc.) and those free from any propellants (set lotions, hair set gels, shampoos, rinses, etc.). It is preferable that the hair care product of the present invention contains a propellant.

It is preferable that a hair care product containing a propellant comprises from 0.01 to 15% (still preferably from 2 to 8%) of the film-forming resin of the present invention, from 50 to 99.8% of solvent(s) selected from among lower alcohols (ethanol, etc.), polyols and water and from 0.1 to 20% of oily component(s) selected from among hydrocarbons, ester oils, silicone and its derivatives and natural fats and oils. In addition, it may contain from 0.5 to 3.0% of texture improver(s) such as higher alcohols, octyldodecyl myristate, glycerol, polyethylene glycol or polyoxyethylene hexadecyl ether and from 0.1 to 3.0% of film-forming aid(s) such as alkylene oxide-addition type alkyl ethers (e.g. polyoxyethylene stearyl ether) or cationic polymers (e.g. cationized cellulose).

Examples of the propellant include LPG, dimethyl ether (DME), flon gas, an LPG/flon mixture and an LPG/DME mixture. Among all, it is particularly preferable to use 50 to 100% LPG gas therefor. In a hair care product of spray type, the ratio of the stock solution to the propellant preferably ranges from 5/95 to 70/30, still preferably from 20/80 to 50/50.

A hair care product in the form of a gel (for example, a hair set gel) preferably contains from 0.5 to 10.0% (still preferably from 1.0 to 3.0%) of the film-forming resin, from 0.5 to 2.0% of thickener(s) selected from water soluble polymers such as polyacrylic acid and hydroxyethylcellulose and purified water optionally together with solvent(s) such as a lower alcohol.

It is also possible to use the film-forming resin of the present invention in shampoos, rinses, etc. In such a case, it is recommended that the content of the film-forming resin ranges from 0.1 to 5.0%, preferably from 0.5 to 2.0%.

Furthermore, these hair care product compositions may contain antiseptics, UV absorbers, sequestering agents, medicinal components (anti-dandruff agents, etc.), coloring matters, perfumes, etc., which are commonly employed in the art, depending on the purpose.

The film-forming resin of the present invention remains tack-free not only under a normal humidity but also under a high humidity and provides the hair care products with an excellent styling power and a lasting set-retaining power. Nevertheless, it can be easily washed away by washing with water or shampooing in a conventional manner, since it carries amino groups which have been neutralized or quaternized and thus is highly soluble in water. Moreover, the film-forming resin of the present invention is highly compatible with LPG. It is highly compatible not only with hydrocarbon solvents (LPG, etc.) but also with various organic solvents including aromatic ones, halogenated ones, ketones, esters, etc. Therefore it can be used in various forms. For example, it is usable as a surface-treating agent for natural leathers, synthetic leathers, rubbers, plastics, glasses, etc. to thereby impart an excellent texture, gloss and luster to the base materials. Also, it can exert antiseptic and antistatic effects, when the composition is appropriately selected. It is also applicable to nail polishes, etc. because of having a good adhesion to proteins such as nail and skin.

To further illustrate the present invention in greater detail, and not by way of limitation, the following Synthesis Examples and Examples will be given.

SYNTHESIS EXAMPLES 1 TO 12

100 parts of ethanol was fed into a four-necked flask provided with a reflux condenser, a dropping funnel, a thermometer, a nitrogen inlet tube and a stirrer. After heating to 60° C., a solution of 100 parts of each monomer as specified in Table 1 dissolved in 200 parts of ethanol (optionally together with water) and a solution of an polymerization initiator dissolved in 33 parts of ethanol were dropped thereinto for 1.5 hours in a nitrogen atmosphere. Then the resulting mixture was allowed to react by maintaining at 60° C. for additional 8 hours. After the completion of the polymerization, the solution of the polymer in ethanol was poured into n-hexane to obtain a purified polymer, which was dried under a reduced pressure (20 mmHg) at 60° C. for 12 hours.

Every polymer thus obtained was in the form of a white solid. The weight-average molecular weight [GPC in a dimethylformamide (DMF) solution: in terms of polyethylene glycol (PEG)] of the polymer of Synthesis Example 1 was 118,900 and those of the polymers of Synthesis Examples 2 to 12 fell within a range of from 70,000 to 200,000.

TABLE 1

| Synthesis Example | 1 | 2 | 3 | 4 | 5 | 6 | 7 | 8 | 9 | 10 | 11 | 12 |
|---|---|---|---|---|---|---|---|---|---|---|---|---|
| Monomer* (wt. %) | | | | | | | | | | | | |
| (1) N-tert-butylacrylamide | 60 | 55 | 55 | 50 | 50 | 60 | 60 | | | 55 | 45 | 65 |
| N-tert-octylacrylamide | | | | | | | | 40 | 50 | | | |
| (2) N,N-dimethylacrylamide | 25 | 30 | | | 30 | 15 | 35 | | 30 | 25 | | |
| N,N-diethylacrylamide | | | | | | | | 36 | | | 25 | |
| N-methylacrylamide | | | 25 | 30 | | | | | | | | |
| (3) N,N-dimethylaminoethyl acrylate | | 5 | 10 | | | | | | | | | |

TABLE 1-continued

| Synthesis Example | 1 | 2 | 3 | 4 | 5 | 6 | 7 | 8 | 9 | 10 | 11 | 12 |
|---|---|---|---|---|---|---|---|---|---|---|---|---|
| N,N-dimetylaminopropylacrylamide | 5 | | | 3 | | 5 | 5 | | 5 | | 10 | 10 |
| N,N-dimethylaminopropylmethacrylamide | | | | | 5 | | | 4 | | 5 | | |
| (4) methoxypolyethylene glycol methacrylate*[1] | 10 | 10 | 10 | 17 | | 20 | | | 15 | | | 15 |
| methoxypolyethylene glycol methacrylate*[2] | | | | | 15 | | | | | 20 | | |
| methoxypolyethylene glycol methacrylate*[3] | | | | | | | | 20 | | | | |
| 2-hydroxyethyl methacrylate | | | | | | | | | | 15 | | |
| Initiator** (mol %) | | | | | | | | | | | | |
| 2,2'-azobis(2,4-dimetylvaleronitrile) (V-65) | 0.2 | 0.2 | 0.2 | 0.2 | 0.2 | 0.2 | 0.2 | | | | 0.2 | |
| azobisisobutyronitrile | | | | | | | | 0.3 | 0.3 | 0.3 | | |

*expressed in % by weight based on the total monomers.
**expressed in % by mol based on the total monomers.
*[1]molecular weight of PEG = 400.
*[2]molecular weight of PEG = 1,000.
*[3]molecular weight of PEG = 600.

SYNTHESIS EXAMPLE 13

Quaternization of amino group:

The monomer mixture of Synthesis Example 1 was dropped for 1.5 hours in the same manner as the one described above. Subsequently, the mixture was allowed to react at 60° C. for 5 hours. Then diethyl sulfate in an amount equivalent to the N,N-dimethylaminopropylacrylamide was dropped into the reaction mixture for 1 hour and the reaction was performed for additional 3 hours. After the completion of the reaction, the product was purified through reprecipitation from hexane and dried at 60° C. under reduced pressure (20 mmHg) for 12 hours. The polymer thus obtained was in the form of a white solid.

The weight-average molecular weight of the polymer of Synthesis Example 13 was 137,000 (GPC in DMF solution, in terms of PEG).

EXAMPLES 1 TO 13

Production of aerosol composition:

In accordance with each composition specified in Table 2, a copolymer was first dissolved in dry ethanol. Then a neutralizing agent, dimethyl polysiloxane (TSF-451-5; manufactured by Toshiba Silicone) and a perfume were added thereto. The solution thus obtained was packed in an aerosol container and then a propellant was pressed thereinto to thereby give an aerosol composition.

TABLE 2

| Synthesis Example | 1 | 2 | 3 | 4 | 5 | 6 | 7 | 8 | 9 | 10 | 11 | 12 | 13 |
|---|---|---|---|---|---|---|---|---|---|---|---|---|---|
| copolymer of Syn. Ex. 1 | 2.5 | | | | | | | | | | | | |
| copolymer of Syn. Ex. 2 | | 2.5 | | | | | | | | | | | |
| copolymer of Syn. Ex. 3 | | | 2.5 | | | | | | | | | | |
| copolymer of Syn. Ex. 4 | | | | 2.5 | | | | | | | | | |
| copolymer of Syn. Ex. 5 | | | | | 2.5 | | | | | | | | |
| copolymer of Syn. Ex. 6 | | | | | | 2.5 | | | | | | | |
| copolymer of Syn. Ex. 7 | | | | | | | 2.5 | | | | | | |
| copolymer of Syn. Ex. 8 | | | | | | | | 2.5 | | | | | |
| copolymer of Syn. Ex. 9 | | | | | | | | | 2.5 | | | | |
| copolymer of Syn. Ex. 10 | | | | | | | | | | 2.5 | | | |
| copolymer of Syn. Ex. 11 | | | | | | | | | | | 2.5 | | |
| copolymer of Syn. Ex: 12 | | | | | | | | | | | | 2.5 | |
| copolymer of Syn. Ex. 13 | | | | | | | | | | | | | 2.5 |
| neutralizing agent | | | | | | | | | | | | | |
| lactic acid | 0.072 | 0.079 | | | 0.066 | 0.072 | | | 0.072 | | | 0.144 | — |
| glycolic acid | | | 0.133 | | | | 0.061 | | | 0.056 | 0.122 | | — |
| dimethylglycolic acid | | | | 0.050 | | | | 0.061 | | | | | — |
| dimethyl polysiloxane | 0.3 | 0.3 | 0.3 | 0.3 | 0.3 | 0.3 | 0.3 | 0.3 | 0.3 | 0.3 | 0.3 | 0.3 | 0.3 |
| perfume | 0.15 | 0.15 | 0.15 | 0.15 | 0.15 | 0.15 | 0.15 | 0.15 | 0.15 | 0.15 | 0.15 | 0.15 | 0.15 |
| dry ethanol*** | balance | — | — | — | — | — | — | — | — | — | — | — | — |
| propellant | | | | | | | | | | | | | |
| LPG | 50 | 50 | 45 | 50 | 50 | 50 | 50 | 50 | 50 | 45 | 50 | 50 | 50 |
| DME | | | 5 | | | | | | | 5 | | | |
| total | 100 | 100 | 100 | 100 | 100 | 100 | 100 | 100 | 100 | 100 | 100 | 100 | 100 |

***"the balance" means a sufficient amount to adjust the total amount excluding the propellant to 50.

COMPARATIVE EXAMPLES 1 TO 4

The procedure of Example 1 was repeated but replacing the copolymer of Synthesis Example 1 employed in Example 1 by the copolymers of Synthesis Examples 1 to 3 in JP-A-2-180911, which had been neutralized with lactic acid at a ratio of 100% (composition ratios of these copolymers are given in Table 3) in Comparative Examples 1 to 3, and a commercially available copolymer of methyl vinyl ether/monobutyl maleate (Gantrez ES425, manufactured by International Specialty Products) in Comparative Example 4 to thereby give each an aerosol composition.

TABLE 3

|  |  | Comparative Example | | |
|---|---|---|---|---|
|  |  | 1 | 2 | 3 |
| (1) | N-tert-butylacrylamide | 55 | 65 | 55 |
| (2) | ethyl acrylate | 25 |  | 25 |
|  | methyl methacrylate |  | 15 |  |
| (3) | N,N-dimethylaminoethyl acrylate | 10 | 10 |  |
|  | N,N-diethylaminoethyl methacrylate |  |  | 10 |
| (4) | methoxypolyethylene glycol (PEG400) methacrylate weight-average molecular weight | 10 104,300 | 10 135,600 | 10 118,400 |

EXPERIMENTAL EXAMPLE

The performances of the aerosol compositions (hair sprays) of Examples 1 to 13 and Comparative Examples 1 to 4 and film-forming resins contained therein were evaluated by the following methods.

(1) Set-retaining power test

A hair bundle (length: 18 cm, weight: 1.5 g) was moistened with water, wound around a rod and then allowed to dry. Then the rod was taken off from the hair bundle thus curled and each composition was sprayed onto the curled hair bundle from four directions. After drying, the curled hair bundle was suspended in a thermo-hygrostat (20° C., 98% R.H.) for 30 minutes and the elongation of the curl was observed to thereby evaluate the set-retaining power. The set-retaining power was judged in the following manner. Namely, the length of the curled hair was measured and the length of the hair immediately after spraying was referred to as a set-retaining power of 100% while that of the uncurled hair bundle (18 cm) was referred to as a set-retaining power of 0%.

Criteria for set-retaining power:

| Rank | Condition |
|---|---|
| ⊚: | 81% or above. |
| O: | 61–80%. |
| Δ | 51 to 60%. |
| x: | 0 to 50%. |

(2) Sensory test on stiffness/tackiness

Each hair spray was sprayed onto a human head model (wig) for laboratory use and the stiffness and tackiness were sensorially evaluated in accordance with the following criteria. Tables 4 and 5 show the results.

Criteria for stiffness and tackiness:
  ⊚: highly superior to control.
  O: somewhat superior to control.
  Δ: comparable to control.
  x: inferior to control.

(3) Hair gloss test

Each hair spray was sprayed onto a human head model (wig) and the conditions of the hair were evaluated with the naked eye in accordance with the following criteria. Tables 4 and 5 show the results.

Criteria for hair gloss:
  ⊚: highly superior to control.
  O: somewhat superior to control.
  Δ: comparable to control.
  x: inferior to control.

(4) Water solubility test

Each hair spray was sprayed onto a glass plate for 3 seconds. The film thus formed was immersed in water for 5 minutes and then the dissolution was evaluated in accordance with the following criteria. Tables 4 and 5 show the results.

Criteria for water solubility/shampoo-washability:
  ⊚: highly superior to control.
  O: somewhat superior to control.
  Δ: comparable to control.
  x: inferior to control.

(5) Shampoo-washability test

The shampoo-washability of each aerosol composition was evaluated by repeating the procedure of the above (4) (water solubility test) but immersing the film formed on the glass plate in a 3% aqueous solution of a shampoo.

TABLE 4

| | Hair spray (Example No.) | | | | | | | | | |
|---|---|---|---|---|---|---|---|---|---|---|
| Evaluation item | 1 | 2 | 3 | 4 | 5 | 6 | 7 | 8 | 9 | 10 |
| (1) set-retaining power | ⊚ | ⊚ | ⊚ | ⊚ | ⊚ | ⊚ | ⊚ | ⊚ | ⊚ | ⊚ |
| (2) tackiness stiffness | ⊚ ⊚ | ⊚ ⊚ | O ⊚ | ⊚ ⊚ | ⊚ ⊚ | ⊚ ⊚ | O ⊚ | O ⊚ | ⊚ ⊚ | ⊚ ⊚ |
| (3) hair gloss | ⊚ | ⊚ | ⊚ | ⊚ | ⊚ | ⊚ | ⊚ | ⊚ | ⊚ | ⊚ |
| (4) water solubility | ⊚ | ⊚ | ⊚ | ⊚ | ⊚ | ⊚ | ⊚ | ⊚ | ⊚ | ⊚ |
| (5) shampoo-washability | ⊚ | ⊚ | ⊚ | ⊚ | ⊚ | ⊚ | O | ⊚ | ⊚ | ⊚ |

TABLE 5

| | Hair spray (Example No.) | | | | | | |
|---|---|---|---|---|---|---|---|
| Evaluation item | 11 | 12 | 13 | C.1 | C.2 | C.3 | C.4 |
| (1) set-retaining power | ⊚ | ⊚ | ⊚ | ⊚ | ⊚ | ⊚ | Δ |
| (2) tackiness stiffness | O ⊚ | O ⊚ | ⊚ ⊚ | x ⊚ | x ⊚ | x ⊚ | x Δ |
| (3) hair gloss | ⊚ | ⊚ | ⊚ | ⊚ | ⊚ | ⊚ | ⊚ |
| (4) water solubility | ⊚ | ⊚ | ⊚ | ⊚ | ⊚ | ⊚ | O |
| (5) shampoo-washability | O | O | ⊚ | x | x | x | O |

As Tables 4 and 5 show, the hair sprays of Comparative Examples 1 to 4 were tacky and those of Comparative Examples 1 to 3 were poor in shampoo-washability. In contrast thereto, the hair sprays of Examples 1 to 13 satisfied both of these requirements at the same time. Moreover, they were excellent in set-retaining power. A product containing a smaller amount of cationic monomers showed the better performance.

FORMULATION EXAMPLE 1

The following components were blended to thereby give a hair-set lotion.

| Component | (%) |
|---|---|
| copolymer of Synthesis Example 1 | 2.0 |
| polyether-denatured silicone (KF-352A, | 1.0 |

| Component | (%) |
|---|---|
| manufactured by Shin-Etsu Chemical Co., Ltd.) | |
| lactic acid | 0.06 |
| ethanol | 86.44 |
| purified water | 10.0 |
| perfume | 0.5 |
| total | 100.0 |

FORMULATION EXAMPLE 2

The following components were blended to thereby give a shampoo.

| Component | (%) |
|---|---|
| lauryl polyoxyethylene sulfate triethanolamine salt (40% aqueous solution, Emul 20C, manufactured by Kao Co.) | 32.0 |
| lauroyldiethanolamide | 4.0 |
| polyethylene glycol (PEG 600, manufactured by Sanyo Chemical Industries, Ltd.) | 1.0 |
| copolymer of Synthesis Example 2 | 1.0 |
| lactic acid | 0.05 |
| purified water | 61.45 |
| perfume | 0.5 |
| total | 100.0 |

FORMULATION EXAMPLE 3

The following components were blended to thereby give a hair gel.

| Component | (%) |
|---|---|
| copolymer of Synthesis Example 2 | 2.0 |
| lactic acid | 0.05 |
| purified water | 80.0 |
| Carbopol 940 (manufactured by B.F. Goodrich) | 0.5 |
| triethanolamine | 0.5 |
| ethanol | 16.75 |
| perfume | 0.2 |
| total | 100.0 |

FORMULATION EXAMPLE 4

The following components were blended to thereby give a hair set foam.

| Composition of stock solution | (%) |
|---|---|
| copolymer of Synthesis Example 1 | 3.0 |
| polyoxyethylene lauryl ether (Emulgen 109P, manufactured by Kao Co.) | 0.5 |
| polyether-denatured silicone (KF-352A, manufactured by Shin-Etsu Chemical Co., Ltd.) | 1.5 |
| ethanol | 10.0 |
| purified water | 84.71 |
| perfume | 0.2 |
| lactic acid | 0.09 |
| total | 100.0 |

Propellant (LPG 100%)
Weight ratio of stock solution/propellant=90/10.

FORMULATION EXAMPLE 5

The following components were blended to thereby give a hair rinse.

| Component | (%) |
|---|---|
| copolymer of Synthesis Example 1 | 1.0 |
| glycolic acid | 0.04 |
| stearyltrimethylammonium chloride | 2.0 |
| cetyl alcohol | 2.0 |
| purified water | 94.76 |
| perfume | 0.2 |
| total | 100.0 |

What is claimed is:

1. A film-forming resin which is a copolymer consisting essentially of:

(a) from 30 to 80% by weight of a (meth)acrylamide monomer represented by the following formula (1):

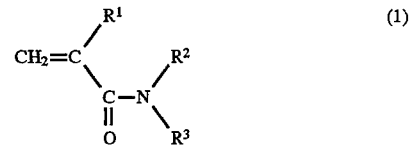

wherein $R^1$ represents a hydrogen atom or a methyl group; and $R^2$ and $R^3$ may be either the same or different and each represents a hydrogen atom or an alkyl group having 4 to 12 carbon atoms, provided that $R^2$ and $R^3$ do not represent hydrogen atoms at the same time;

(b) from 2 to 50% by weight of a (meth)acrylamide monomer represented by the following formula (2):

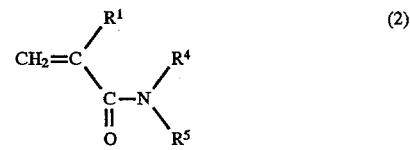

wherein $R^1$ is as defined above; and $R^4$ and $R^5$ may be either the same or different and each represents a hydrogen atom or an alkyl group having 1 to 3 carbon atoms;

(c) from 0.5 to 30% by weight of a (meth)acrylate monomer or a (meth)acrylamide monomer represented by the following formula (3):

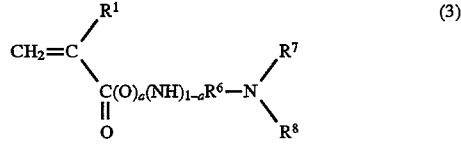

wherein $R^1$ is as defined above; $R^6$ represents an alkylene group having 2 or 3 carbon atoms; $R^7$ and $R^8$ may be either the same or different and each represents a methyl group or an ethyl group; and $a$ represents a number of 0 or 1; and (d) from 0 to 40% by weight of a (meth)acrylate monomer represented by the following formula (4):

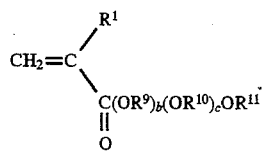 (4)

wherein $R^1$ is as defined above; $R^9$ and $R^{10}$ may be either the same or different and each represents an alkylene group having 2 to 4 carbon atoms; $R^{11}$ represents a hydrogen atom, an alkyl group having 1 to 10 carbon atoms or a phenyl group; and b and c represent each a number of from 0 to 50, provided that b and c do not represent 0 at the same time.

2. A film-forming resin as claimed in claim 1, wherein at least 50% of the tertiary amino groups in said copolymer have been neutralized with an inorganic acid or an organic acid or quaternized with a quaternizing agent.

3. A hair care product comprising a film-forming resin as claimed in claim 1 or 2.

4. A hair care product as claimed in claim 3 wherein said hair care product comprises a propellant as delivery device.

5. A method for hair care, comprising the step of applying an effective film-forming amount of the film-forming resin of claim 1 to hair.

* * * * *